United States Patent
Guo

(10) Patent No.: US 10,353,124 B1
(45) Date of Patent: Jul. 16, 2019

(54) OMNI-DIRECTIONAL ULTRA-THIN REFLECTION OPTICAL FILTERS AND METHODS OF FABRICATION

(71) Applicant: Junpeng Guo, Madison, AL (US)

(72) Inventor: Junpeng Guo, Madison, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 54 days.

(21) Appl. No.: 15/404,000

(22) Filed: Jan. 11, 2017

Related U.S. Application Data

(63) Continuation-in-part of application No. 14/885,843, filed on Oct. 16, 2015.

(51) Int. Cl.
  *G02B 5/20* (2006.01)
  *G02B 5/28* (2006.01)

(52) U.S. Cl.
  CPC ............ *G02B 5/288* (2013.01); *G02B 5/207* (2013.01)

(58) Field of Classification Search
  CPC . G02B 5/22; G02B 5/26; G02B 5/265; G02B 5/288; G01J 3/26
  USPC ................. 359/885, 359, 360, 589, 586–588
  See application file for complete search history.

(56) References Cited

U.S. PATENT DOCUMENTS

| | | | | |
|---|---|---|---|---|
| 2013/0148221 A1* | 6/2013 | Banerjee et al. | ........ | G02B 5/22 |
| 2013/0265668 A1* | 10/2013 | Banerjee et al. | ........ | G02B 5/22 |
| 2016/0160364 A1* | 6/2016 | Juluri et al. | ............ | C25B 11/04 |

OTHER PUBLICATIONS

Guo, et al., U.S. Appl. No. 14/885,843, entitled, "Silicon Optical Filters Systems and Methods of Fabrication," filed Oct. 16, 2015.
(Continued)

*Primary Examiner* — Thanh Luu
(74) *Attorney, Agent, or Firm* — Maynard Cooper & Gale, P.C.; Jon E. Holland

(57) ABSTRACT

A reflection optical filter has an ultra-thin semi-transparent layer and a thin layer of semiconductor (or dielectric) layer deposited onto a metal film surface at a certain thickness corresponding to a wavelength of light to be filtered from incoming light. Critical coupling of light to the optical cavity formed by the semi-transparent layer and semiconductor (or dielectric) layer on metal surface results in near perfect absorption of the light at one wavelength and strong absorption in the wavelength region near the peak absorption wavelength. Incoming lights of other wavelengths are mostly reflected by the device so the spectral content of incident light is changed. By controlling the thickness of the semiconductor (or dielectric) layer and/or other factors, such as the extent to which the semiconductor layer is annealed or changing the type of metal beneath the semiconductor (or dielectric) layer, the peak absorption wavelength of the light absorbed in the device can be precisely controlled. The overall thickness of the semi-transparent layer and semiconductor (or dielectric) layer is less than one order of magnitude of the wavelength to be filtered, which results in omni-directional performance of the optical filter.

22 Claims, 11 Drawing Sheets

(56) References Cited

OTHER PUBLICATIONS

World News, "Thin-Film Filters," Laser Focus World, www.laserfocusworld.com, p. 24, Jan. 2015.

Lipson, et al., "Low Loss Tunable Optical Filter Using Silicon Photonic Band Gap Mirrors," Proc. Transducers 2007, pp. 1445-1448, Jun. 10-14, 2007.

* cited by examiner

OMNI-DIRECTIONAL ULTRA-THIN REFLECTION OPTICAL FILTERS AND METHODS OF FABRICATION

CROSS REFERENCE TO RELATED APPLICATION

This application is a continuation-in-part of and claims priority to U.S. patent application Ser. No. 14/885,843, entitled "Silicon Optical Filters Systems and Methods of Fabrication" and filed on Oct. 16, 2015, which is incorporated herein by reference.

STATEMENT REGARDING FEDERALLY SPONSORED RESEARCH OR DEVELOPMENT

This invention was made with Government support under contract 2014-67022-21618 awarded by the United States Department of Agriculture. The Government has certain rights in the invention.

RELATED ART

A variety of applications require devices that display colors vibrantly and accurately in ambient light. It is often desirable for the wavelengths of light absorbed (and reflected) by a device to remain constant, when viewed from a wide range of viewing angles. Conventional optical filters capable of achieving this effect are often expensive and complex.

In conventional low-cost optical filters, distortion of reflected wavelengths often varies with the angle of incidence. Thus, the desired color is accurately reflected only for a limited range of reflection angles. Improved low-cost optical filters capable of accurately reflecting a desired wavelength range across a wide range of angles are generally desired.

In addition, coloring applied to a material using conventional techniques may be compromised in under extreme conditions or in harsh environments. Dyes and other methods of coloring a material generally break down, and coloring of the material may be permanently altered or destroyed. Improved optical filters capable of withstanding extreme environmental conditions while maintaining optical integrity thus may generally be desirable.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
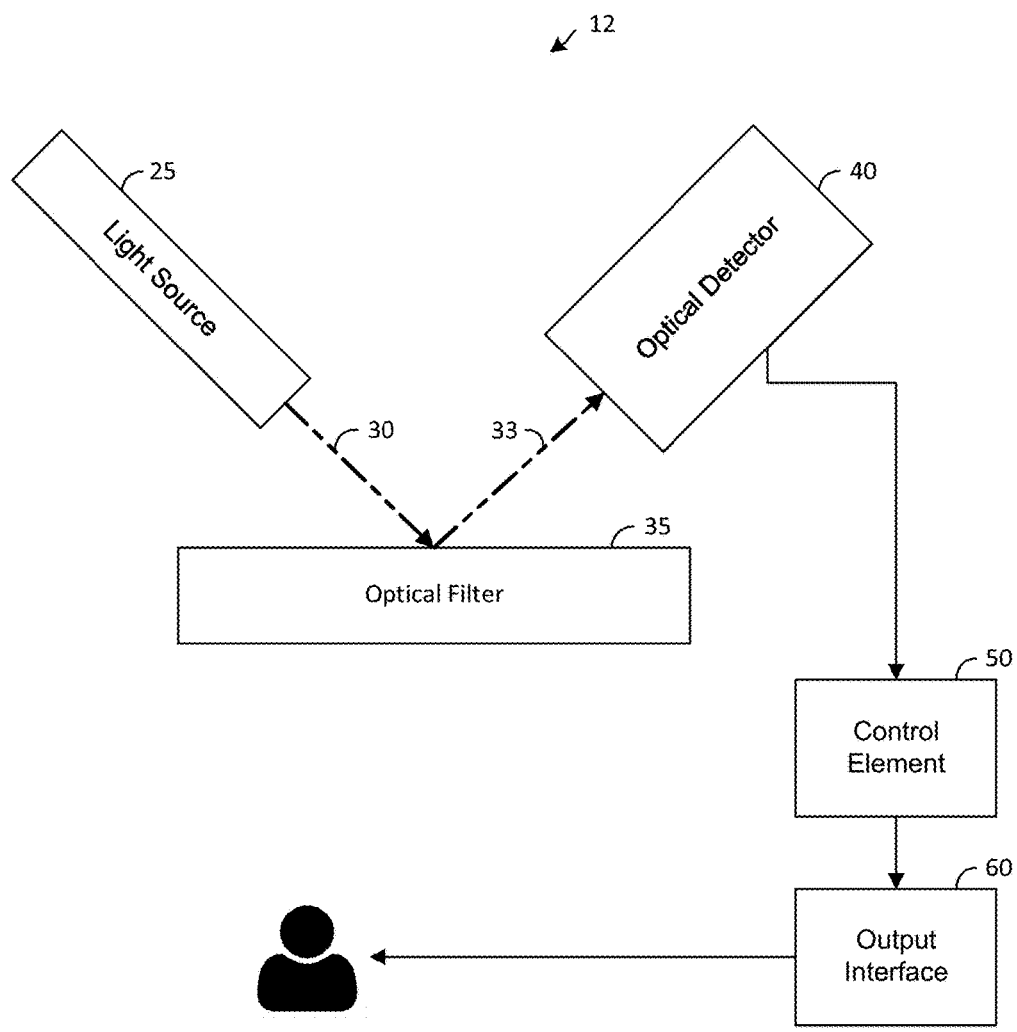
FIG. 1 depicts an exemplary embodiment of an optical filtering system.

The present disclosure generally pertains to optical filtering systems and methods. A reflection optical filter in accordance with an exemplary embodiment has a layer of silicon film deposited onto a metallic substrate at a thickness corresponding to a wavelength of light to be filtered from incoming light. If desired, thermal annealing of the silicon film may be performed for precisely tuning the center of the absorption peak. During operation, a light source emits light toward the silicon film. The thickness of the silicon film is selected to achieve near perfect absorption of the incoming light into the silicon film at a particular wavelength. Other wavelengths of the incoming light are reflected by the silicon film such that the reflected light has an absorption peak centered about the particular wavelength, referred to hereafter as the "center wavelength." An optical detector detects the reflected light and generates a signal that is indicative of the light detected. A control element receives the signal from the optical detector and provides an output that is indicative of the light detected by the optical detector. The control element communicates the output to an output device, which displays the output to a user. By controlling the thickness of the silicon film and/or other factors, such as the extent to which the silicon film is annealed or the type of metal beneath the silicon film, the center wavelength of the light absorbed by the silicon film can be precisely controlled.

It has been observed that silicon film can be used to realize spectral-selective near perfect light absorption where critical coupling conditions occur to one of the optical resonance modes of a silicon film optical cavity. Silicon is a low cost material that is widely used in the electronics industry. Additionally, silicon has the smallest optical extinction coefficient among commonly used high-index semi-conductive materials in the range of visible light wavelengths. "Near perfect" absorption of light by an optical filter generally refers to spectrally selective absorption of incoming light where greater than 95% of the incoming incident light energy at the selected wavelength is absorbed. Experiments have shown that absorption rates close to 100% (e.g., greater than 98%) can be achieved through the use of silicon films, as described herein. In addition, the optical reflectance of the silicon film is angle-insensitive, this results in colors that remain unchanged when viewed from different angles, even at large angles of incidence with regard to the surface normal of the silicon film.

A single layer of silicon film on a metal surface can function as an optical cavity (e.g., an asymmetric Fabry-Perot) for achieving near perfect light absorption. The peak absorption wavelength can be altered by varying the silicon film's thickness. Increasing a silicon film's thickness allows for additional resonance modes to occur in the optical cavity. Importantly, it has been observed that near perfect light absorption occurs in the silicon-on-metal optical cavity at the critical coupling condition met by one of the optical resonance modes. Light absorption occurs for other resonance modes, but not necessarily near perfect light absorption. Thus, the thickness of the silicon film is preferably sufficient to meet the critical coupling condition of a desired optical resonance mode.

As noted above, the peak wavelength of light absorbed by the silicon thin-film on metal optical cavity can be altered (e.g., tuned) by varying the thickness of a silicon film. By increasing the silicon thickness, the peak absorption wavelength generally shifts to a longer wavelength. It has further been observed that the peak wavelength of light absorbed by silicon films can be shifted by subjecting the silicon films to thermal annealing. Thermal annealing (e.g., using a furnace) of the silicon film for a period of time changes a silicon film from an amorphous phase to a polycrystalline phase. It has been observed that changing silicon's phase from amorphous to polycrystalline significantly reduces the imaginary part of the silicon film's refractive index. This results in a shift in wavelengths of light absorbed by the silicon thin-film toward a shorter wavelength (e.g., produces "blue-shifts" in the peak wavelength absorbed). The change of silicon from amorphous phase to polycrystalline or crystalline phase changes the silicon's refractive index.

Silicon and metal films can be deposited onto a metal surface using a variety of techniques. For example, amorphous silicon film and metal film may be deposited onto various surfaces using a sputter machine. Using this technique, thickness of the silicon film (and, thus, wavelength of light absorbed by it) can be controlled by varying sputtering time. In this regard, a single layer of silicon film can be deposited onto a variety of metal film surfaces. Silicon films can be deposited using a sputter onto soft, hard, curved, flat, smooth or rough substrates. Thus, optical filtering using silicon films is possible for a wide variety of applications. Since silicon is used to from the resonant cavity, the filter can be better resistant to higher temperatures. Indeed, the materials can be selected so that the filter is capable of withstanding temperatures up to about 500° C., which is much greater than chemical dyes.

Silicon films offer a robust alternative to traditional optical filters and coloring methods that are expensive and have use in limited applications. First, low cost and abundant supply of silicon makes it ideal for widespread use as an optical filter material. Traditional optical filters are expensive and burdensome to manufacture. Additionally, inherent properties of silicon give it an advantage over conventional coloring methods. For example, high temperature tolerance of silicon films (from about −250° Celsius (C) to about 500° C.) makes it an ideal alternative to conventional chemical dyes that are unable to withstand similarly high temperatures. Thus, use of silicon films as spectral-selective light absorbers allows for use in a variety of applications, such as low cost optical filters, enhanced photodetectors, solar cells and colorimetric biochemical sensors.

FIG. 1 depicts an exemplary embodiment of an optical filtering system 12. The system 12 has a light source 25 for generating and outputting light 30 and a reflection optical filter 35 for filtering incident light from the light source 25 by absorbing at least one wavelength of the light 30. Light not absorbed by the optical filter 35 is reflected as reflected light 37. This light 37 reflected by the optical filter 35 is detected by an optical detector 40. The optical detector 40 communicates a signal to a control element 50 that generates an output (e.g., a message, data, or image) indicative of the reflected light 37 detected by the optical detector 40. The control element 50 then communicates the output to an output interface 60, which displays or otherwise renders the output. As an example, the output may define a message that specifies or otherwise indicates the wavelength at the center of the absorption peak in the reflected light 37. In another example, the output may define an image captured by the optical detector 40.

In an exemplary embodiment, the light source 25 of the system 12 is configured to emit light and comprises an unpolarized broadband halogen light source. That is, light 30 generated by the light source 25 is unpolarized. Other light sources 25 are possible in other embodiments. Note that the light source 25 shown by FIG. 1 emits light 30 in at least the visible spectral range of wavelengths. In other embodiments, the light source 25 may be configured to emit light 30 in other spectral ranges (e.g., infrared and ultraviolet spectral ranges).

Note that the use of a light source 24 and an optical detector 40 is unnecessary. For example, the optical filter 35 may filter ambient light that is incident on the surface of the filter 35, which changes the color of the reflected light for observation by a human. Thus, the optical filter 35 may be positioned on the surface of an object in order to change the color of the object perceived by a human. Other uses of the filter 35 are possible in other embodiments.

The optical filter 35 shown by FIG. 1 is configured to absorb at least one wavelength of the light 30. The optical filter 35 has a silicon thin-film (not specifically shown in FIG. 1) positioned on its surface and exposed to incident light 30 emitted by the light source 25, as discussed at length below. As the light 30 becomes incident on the silicon thin-film surface (not specifically shown in FIG. 1) of the optical filter 35, light of at least one wavelength is absorbed by the silicon thin-film structure. The light that is not absorbed is instead reflected by the optical filter 35 (e.g., the silicon thin-film surface, not specifically shown in FIG. 1) as reflected light 37. Note that the reflected light 37 shown in FIG. 1 does not include all of the wavelengths found in the light 30 because the optical filter 35 has absorbed at least one peak wavelength. In this regard, the reflected light 37 has an absorption peak centered about a specific wavelength, referred to as the "center wavelength" of the absorption peak.

FIG. 1 further depicts an optical detector 40 for generally detecting reflected light 37. In one embodiment, the optical detector 40 comprises an optoelectronic sensor, but other devices suitable for detecting light as required herein are possible in other embodiments. A single optical detector 40 is shown by FIG. 1, but the system 12 may comprise any number of optical detectors 40 in other embodiments.

The optical detector 40 is coupled to a control element 50. In an exemplary embodiment, the control element 50 communicates with and generally controls the functions of the optical detector 40. The control element 50 may be implemented in hardware or a combination of hardware and software. In some embodiments, the control element 50 may comprise software running on an instruction execution apparatus, such as a digital signal processor (DSP) or central processing unit (CPU). In such embodiment, the software may be stored in memory (not shown). Note that the control element 50 and optical detector 40 may comprise wireless communication interfaces (not specifically shown) for communicating wirelessly with one another. Alternatively, the control element 50 and the optical detector 40 may be coupled to one another via one or more physical connections (e.g., electrical or optical) for permitting communication between the control element 50 and the optical detector 40.

The optical detector 40 is configured to generate a signal that is indicative of light detected by the optical detector 40 and communicate the signal to the control element 50. In one embodiment, the control element 50 is configured to receive a signal from the optical detector 40 and calculate or otherwise determine a parameter indicative of the light detected by the optical detector 40. As an example, the control element 50 may determine the center wavelength of an absorption peak in the light or the boundary wavelengths of such absorption peak. Alternatively, the control element may determine the color of the detected light or capture an image of the detected light. As shown by FIG. 1, the control element 50 is coupled to an output interface 60 that is configured display information indicative of the parameter or the color(s) determined by the control element 50. As an example, the display may include data indicating which wavelength(s) have been absorbed or the colors of light that are detected, or the display may define an image captured by the optical detector 40.

In the exemplary embodiment shown by FIG. 1, the angle of incidence for the light 30 emitted by the light source 25 as shown by FIG. 1 is approximately 30° from the surface normal of the silicon film 35, although other angles in other embodiments are possible. Near perfect light absorption by the optical filter 35 results in consistent light reflection across a wide range of viewing angles. That is, the color of light reflected by the optical filter is angle-insensitive for a large range of angles. In this regard, it has been observed that the wavelength of reflected light 33 detected by the optical detector 40 will remain substantially constant at angles of incidence of up to 60° or more with respect to a line normal to the surface of the optical filter 35. Thus, the optical filter 35 appears to maintain approximately the same color when viewed at angles that otherwise may result in distortion of reflected wavelengths in conventional optical filters.

Figure 2A:
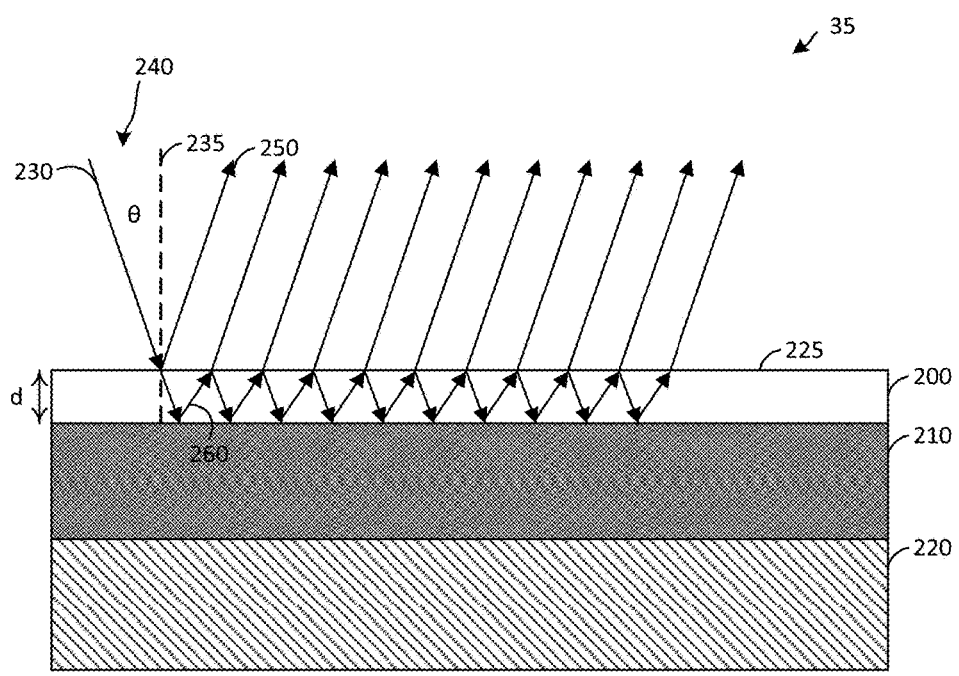
FIG. 2A is a cross sectional view depicting an exemplary embodiment of a reflection optical filter, such as is depicted by FIG. 1.

FIG. 2A is a cross sectional view depicting an exemplary embodiment of a reflection optical filter 35. As shown by FIG. 2A, the optical filter 35 has a thin film 200 that is deposited on a surface of an opaque metal substrate 210. In an exemplary embodiment, the thin film 200 is composed of silicon-based material, such as pure silicon or a combination of silicon and other elements, and the substrate 210 may be composed of a metal, such as aluminum. In other embodiments, the thin film 200 may be composed of other semiconductor materials. The metal substrate 210 is thick enough to block the light transmission through it. Unless otherwise indicated, it will be assumed hereafter that the silicon thin film 200 is composed of pure silicon and that the substrate 210 is composed of aluminum, but it should be emphasized that other types of materials (e.g., gold, silver etc.) or combinations of materials are possible in other embodiments. Further, it is possible for the substrate 210 to be composed of materials other than metals.

In an exemplary embodiment, the silicon thin-film 200 has a thickness between about 110 nanometers (nm) and 140 nm, though other thicknesses of the silicon thin-film 200 are possible in other embodiments. In the instant embodiment, the aluminum substrate 210 has a thickness of about 300 nm, although other thicknesses are possible, and is deposited onto a substrate 220. In one embodiment, the substrate 220 is composed of glass, and the thickness of the substrate 220 is about 4 inches. However, other types of materials (e.g., plastics) and thicknesses are possible in other embodiments. Note that the aluminum substrate 210 is thick enough to block light transmission (i.e., light is reflected). Additionally, as noted hereinabove, the silicon thin-film 200 may be deposited on a surface of other materials, and it is not necessary for the optical filter 35 to comprise an aluminum substrate 210 and glass substrate 220 in other embodiments.

An upper face 225 of the silicon thin-film 200 is exposed to light, such as light emitted by the light source 25 of FIG. 1. In the exemplary embodiment shown by FIG. 2A, an incident light wave 230 makes contact with the surface 225. In the context of this document, the angle at which an incident light 230 makes contact with a surface 225 relative to a line 235 normal to such surface is referred to as an angle of incidence 240. That is, the angle of incidence 240 is the angle formed between the direction of propagation of the incident light wave 230 and a line 235 that is normal to the surface 225 of the optical filter 35.

FIG. 2A further depicts reflected light 250. The reflected light 250 depicted by FIG. 2A has been reflected by the surface 225 of the silicon thin-film 200 or exits the silicon thin-film 225 after reflecting from the layer 210. Note that less than all of the light is reflected by the surface 225. In this regard, light at a certain wavelength corresponding to the thickness of the silicon thin-film 200 is absorbed into the filter 35. Specifically, the absorbed light 260 propagates through the silicon thin-film 200 and reflects off of the surface of the aluminum substrate 210. As shown by FIG. 2A, the absorbed light 260 continues to reflect between the upper surface of the substrate 210 and the upper surface of the silicon thin-film 200 until the energy of the absorbed light 260 is dissipated. Note that at each reflection point, a very small portion of the light 260 may escape from the silicon thin-film (e.g., absorb into the aluminum substrate 210 for a lower reflection point or pass through the upper surface of the silicon thin-film 200 into the surrounding environment (e.g., air) for an upper reflection point).

The propagation of light through the silicon thin-film 200 produces standing waves in the silicon thin-film for certain resonant frequencies. The standing wave patterns produced are generally referred to as "modes." The resonance enhances optical interference at wavelengths corresponding to the resonant frequencies, thereby causing the silicon thin-film 200 to absorb a greater amount of light at such wavelengths. Near perfect absorption is achieved for the wavelength corresponding to the second order optical resonance mode of the film 200, which is based on the thickness d of the film 200, as well as other factors such as the extent to which the film 200 has been annealed. Thus, the reflected light 250 includes an absorption peak centered about the foregoing wavelength, referred to as the "center wavelength" of the absorption peak.

As shown by FIG. 2A, no light from the incident light 230 passes completely through the aluminum substrate 210, though it is possible for light to pass completely through the substrate 210 in other embodiments. The peak wavelength of light absorbed varies as a function of the thickness d of the silicon thin-film 200, which in turn alters the optical resonance modes that occur within the thin film 200. As noted above, near perfect optical absorption in the visible optical spectrum range occurs via the critical coupling condition when the thin film 200 is thick enough to accommodate second mode optical resonance. In one embodiment, the silicon thin-film 200 has a thickness between about 110 nm and 140 nm, but other thicknesses of the silicon thin-film 200 are possible in other embodiments. Varying the thickness of the silicon thin-film 200 within such range causes the absorption peak to shift such that the wavelength at the absorption peak can be controlled by controlling the thickness of the silicon thin-film 200. Note that an absorption peak may also be shifted by annealing the silicon thin-film 200. Thus, the absorption peak wavelength may be tuned through selection of the thickness of the silicon thin-film 200 and annealing of the silicon thin-film 200 as may be desired. Further, as will be described in more detail below, light may slightly penetrate the surface of the metal substrate 210, thereby increasing the distance that the light penetrates the filter 35 and altering the optical resonance wavelength within the silicon thin-film cavity. Thus, tuning of the absorption peak may also be achieved through selection of the material for the metal film 210.

Figure 2B:
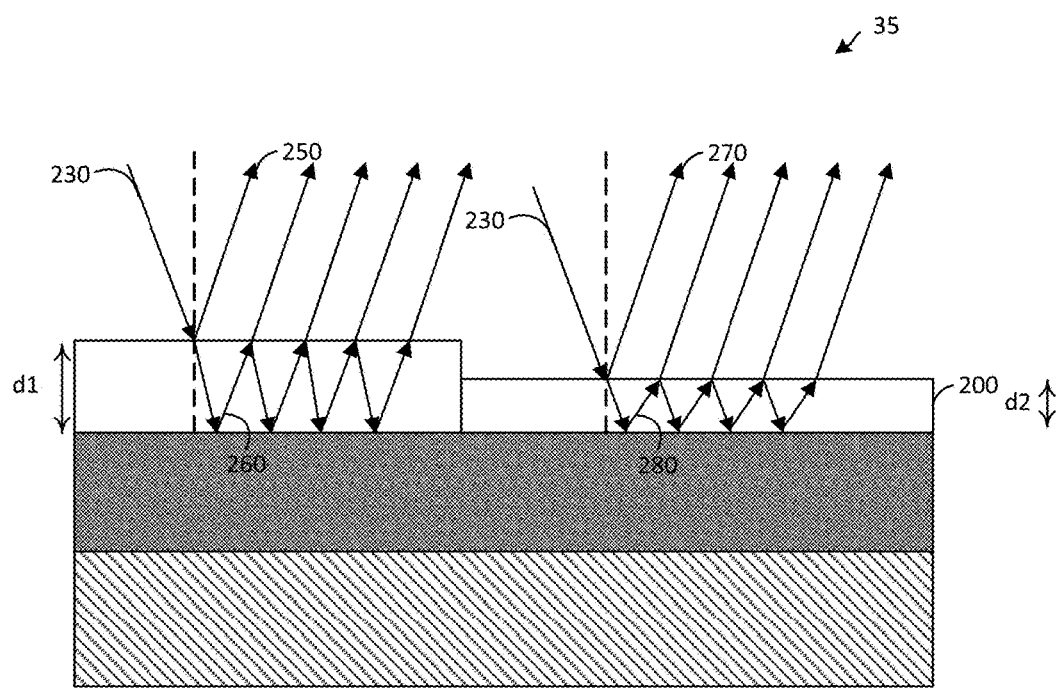
FIG. 2B is a cross sectional view depicting an exemplary embodiment of a reflection optical filter, such as is depicted by FIG. 1.

FIG. 2B is a cross-sectional view depicting an exemplary embodiment of a reflection optical filter 35. In some embodiments, the thickness of the silicon thin-film 200 may be varied across the width of the filter 35 for creating multiple absorption peaks, and thus, reflecting any desired set of wavelengths. In the embodiment shown by FIG. 2B, the silicon thin-film 200 has thicknesses d1 and d2, where d1 is not equal to d2, and both d1 and d2 are sufficiently large to achieve the critical coupling condition of the optical resonance mode for incident light 230. As incident light 230 makes contact with the optical filter 35, the portion of the optical filter 35 having a silicon thin-film 200 of thickness d1 absorbs light 260 with an absorption peak at a first wavelength. Concurrently, the portion of the optical filter 35 having a silicon thin-film 200 of thickness d2 absorbs light 280 with an absorption peak at second wavelength different than the first wavelength. Thus, light reflecting from the surface of the portion of the silicon thin-film 200 having a thickness d1 may exhibit a different color than light reflecting from the surface of the portion of the silicon thin-film 200 having a thickness d2. Thus, the silicon thin-film 200 may be patterned with different thicknesses to define a desired image where any portion of the surface of the silicon thin-film may exhibit a different color relative to any other portion. Any silicon thin-film may be divided into any number of different portions having different thicknesses in order to define any desired pattern for the image reflected by the silicon thin-film 200. Thus, the optical filter can be configured to achieve near perfect absorption of any set of wavelengths such that the spectrum of the reflected light can be tailored as may be desired to achieve a certain overall color.

Note that varying the thickness of silicon thin-film 200 across the filter may be achieved by varying sputtering time when the silicon thin-film 200 is deposited or by etching of the silicon thin-film 200 after it has been deposited onto the substrate 210. In this regard, it is possible to create color patterns by varying the thickness (e.g., by having different thicknesses of the film 200 on different portions of the surface of optical filter 35) of the silicon thin-film 200 that is deposited on the surface of the aluminum substrate 210. Note also that the silicon thin-film 200 shown by FIGS. 2A and 2B may be thermally annealed to shift any absorption peak, but it is not necessary to perform thermal annealing on the silicon thin-film 200 in all embodiments.

In addition, as described above, it is possible to tune the absorption peak in the reflected light 250 through annealing. Thus, it is possible to create a pattern in the surface of the silicon thin-film, as described above with reference to FIG. 2B, by annealing different portions of the silicon thin-film differently rather than changing the thicknesses of the two portions. By annealing one portion of the silicon thin-film 200 differently than another portion, the light reflected by each portion may have a different color. If desired, a combination of controlling the thicknesses of different portions of the silicon thin-film 200 differently and annealing different portions of the silicon thin-film differently may be performed in order to define any type of image on the surface of the silicon thin-film 200 as may be desired.

Figures 3A, 3B:
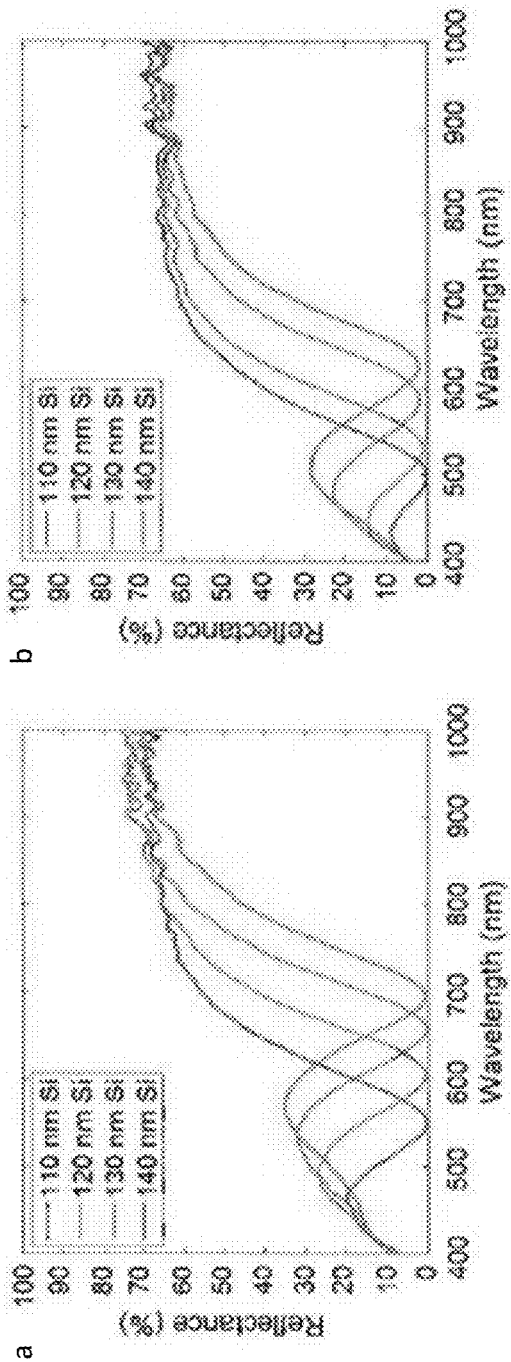
FIG. 3A is a plot illustrating exemplary measurements of reflectance of light at a variety of wavelengths by optical filters having silicon films of varying thicknesses.
FIG. 3B is a plot illustrating exemplary measurements of reflectance of light at a variety of wavelengths by optical filters having thermally annealed silicon films of varying thicknesses.

FIG. 3 depicts a plot illustrating exemplary measurements of absorption occurring at various wavelengths for silicon thin-film. The exemplary measurements of FIG. 3 include measurements for silicon films of thicknesses 110 nm, 120 nm, 130 nm, and 140 nm. As shown by FIG. 3A, critical coupling resulting in near perfect optical absorption (e.g., zero reflectance) occurs for each thickness of silicon film listed. Note that critical coupling condition is a condition in which the optical power coupled when light becomes incident on the surface of the silicon thin-film equals the optical loss per resonance cycle in the optical cavity (here, the silicon thin-film). Stated differently, "critical coupling" refers to a condition at which the light penetrating through to an optical cavity is completely absorbed in the cavity. The second order resonance mode of the thin film optical cavity can meet this critical coupling condition because of increased silicon film thickness. The second order optical resonance mode appears in a visible spectral range when the silicon thin-film thickness increases above 90 nm. As depicted by FIG. 3, at the second order optical resonance mode for silicon film thicknesses from 110 nm to 140 nm, critical coupling conditions can be met and near perfect light absorption occurs in the optical wavelength ranges from about 552 nm to about 700 nm. Note that the absorption wavelengths for the exemplary measurements shown by FIG. 3A are approximately 552 nm, 605 nm, 657 nm, and 700 nm for silicon thin-films with thicknesses of approximately 110 nm, 120 nm, 130 nm, and 140 nm, respectively. As demonstrated by the exemplary measurements of FIG. 3A more than approximately 99% optical absorption occurs within a spectral reflective optical filter using silicon thin-film at the second order optical resonance wavelengths in the silicon thin-film's amorphous state. Note also that first and third order optical resonance modes do not likely result in complete absorption in the thin-film cavity because the critical condition is not likely met.

FIG. 3B depicts a plot showing exemplary measurements of optical reflectance following thermal annealing of a silicon thin-film at thicknesses of approximately 110 nm, 120 nm, 130 nm, and 140 nm. As also depicted by FIG. 3A, exemplary measurements of FIG. 3B reflect near perfect optical absorption for a variety of wavelengths. However, for silicon thin-films with thicknesses of approximately 110 nm, 120 nm, 130 nm, 140 nm, the exemplary measurements of FIG. 3B demonstrate absorption wavelengths exhibiting "blue shifts". This results in absorption at peak wavelengths of about 500 nm, 531 nm, 587 nm, and 625 nm respectively. For the thicknesses ranging between approximately 110 nm 140 nm, optical absorption in annealed silicon films exceeds about 98%.

Figure 4:
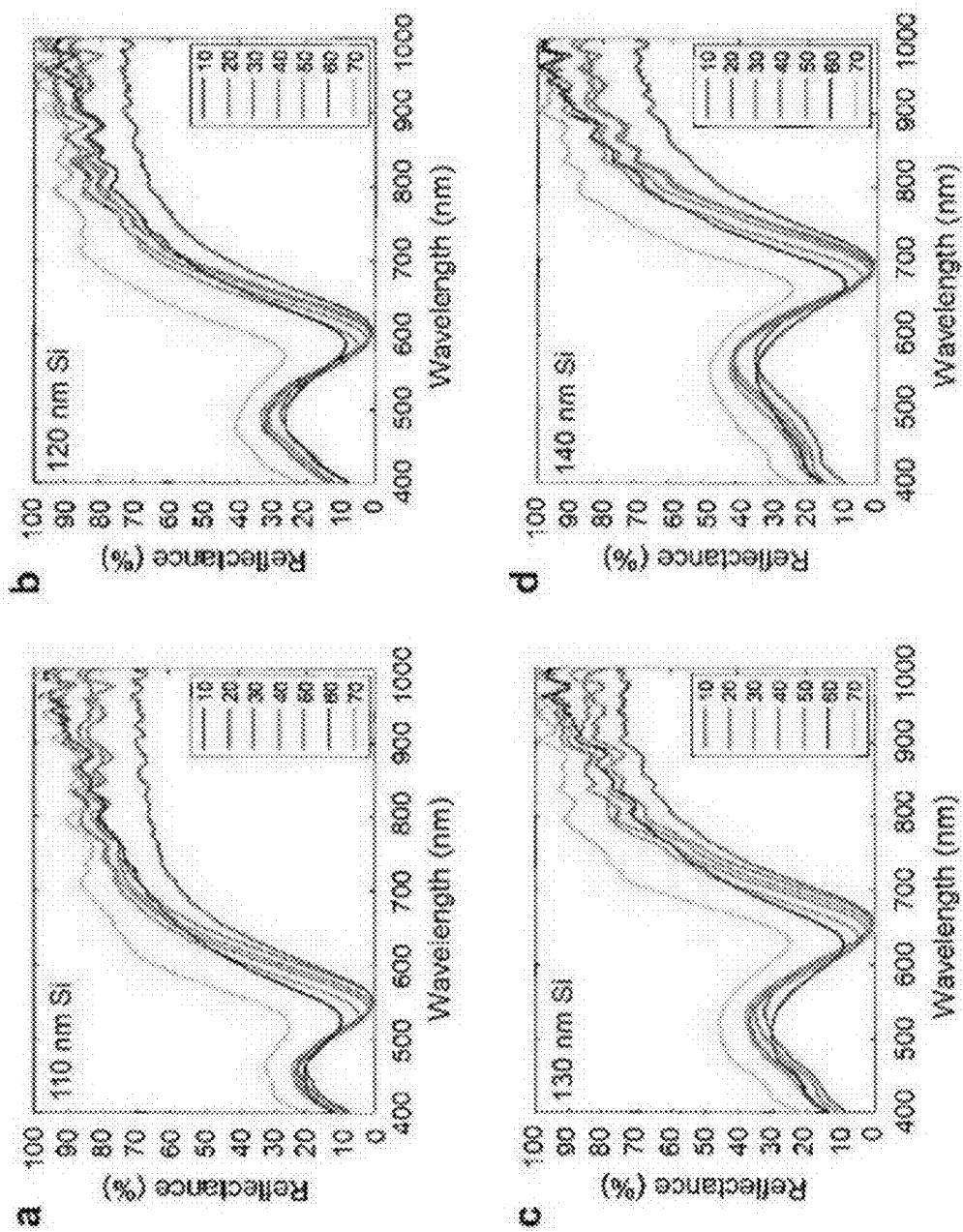
FIG. 4 depicts plots illustrating exemplary measurements of reflectance of light with incrementally-increasing incidence angles at a variety of wavelengths by a reflection optical filter with a silicon thin-film having a thickness between about 110 nanometers and 140 nanometers.

FIG. 4 depicts a series of plots of exemplary measurements of reflectance of varying thicknesses of silicon thin-films when viewed at angles incremented by 10°. As noted above, use of silicon thin-films as a reflection optical filter results in reflectance of light that is angle-insensitive across a wide a range of angles. FIG. 4 demonstrates that the wavelength at which peak absorption occurs in the silicon thin-film shifts to slightly shorter wavelengths as the angle of incidence increases. Likewise, the reflection peak wavelength does not exhibit distortion as the incident angle increases to 60°. In this regard, the exemplary measurements of FIG. 4 illustrate that peak wavelengths absorbed by the silicon thin-film remain constant, so that the color of the silicon thin film remains essentially unchanged, even when viewed from varying angles relative to the surface normal of the silicon thin-film.

Figure 5:
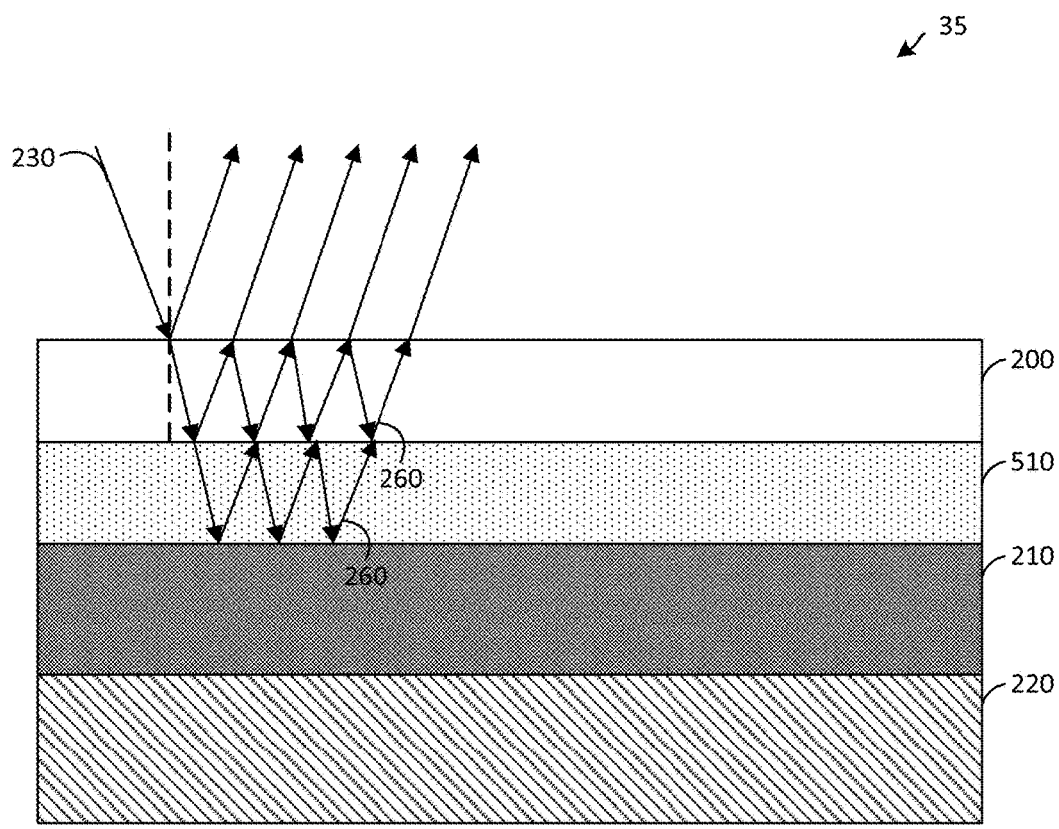
FIG. 5 is a cross sectional view depicting an exemplary embodiment of a reflection optical filter having a layer comprising a semiconductor or dielectric film.

FIG. 5 depicts a cross sectional view of an exemplary embodiment of a reflection optical filter 35 that is the same as the filter 35 shown by FIG. 2A except that the filter 35 of FIG. 5 has an additional layer 510 between the silicon thin-film 200 and the metal substrate 210. In one embodiment, the layer 510 is composed of a dielectric material, but other types of materials are possible in other embodiments. The addition of a transparent dielectric layer 510 between a layer of a silicon thin-film 200 and opaque metal layer 210 can achieve a narrower absorption peak than can be achieved by use of a silicon thin film 200 alone. That is, the spectral width of the absorption peak is reduced by the presence of the dielectric layer 510. In this regard, the dielectric layer 510 has a lower absorption loss coefficient in visible light frequencies than does the layer of silicon thin-film 200. This permits the absorbed light 260 to reflect back and forth between the silicon thin-film 200 and the substrate 210 longer (i.e., a greater number of times), thereby enhancing the optical interference occurring in the silicon thin-film. Thus, near perfect absorption can be achieved with a narrower absorption peak in the reflected light 250.

As noted above, the peak absorption wavelength may be tuned by altering the thickness of the silicon thin-film 200 or by annealing. As also described above, it has also been observed that the peak absorption wavelength of the optical filter 35 may be tuned through selection of the material of the metal substrate 210. Thus, it is possible to divide the substrate 210 into different types of metal materials in order to control a pattern of the image reflected off of the surface of the silicon thin-film 200, similar to the pattern described above for FIG. 2B. In this regard, by forming one portion of the silicon thin-film 200 on a metal different than the metal on which another portion of the silicon thin-film 200 is formed, the light reflected by each portion may have a different color. Thus, the colors reflected by the surface of the silicon thin-film 200 can be controlled across the face of the thin-film 200 without altering the thickness of the film 200 or annealing the film 200. If desired, a combination of controlling the thicknesses of portions of the silicon thin-film 200 differently, annealing portions of the silicon thin-film 200 differently, and/or forming portions of the silicon thin-film 200 on different types of materials (e.g., different metals) may be performed in order to define any type of image on the surface of the silicon thin-film 200 as may be desired.

Figure 6:
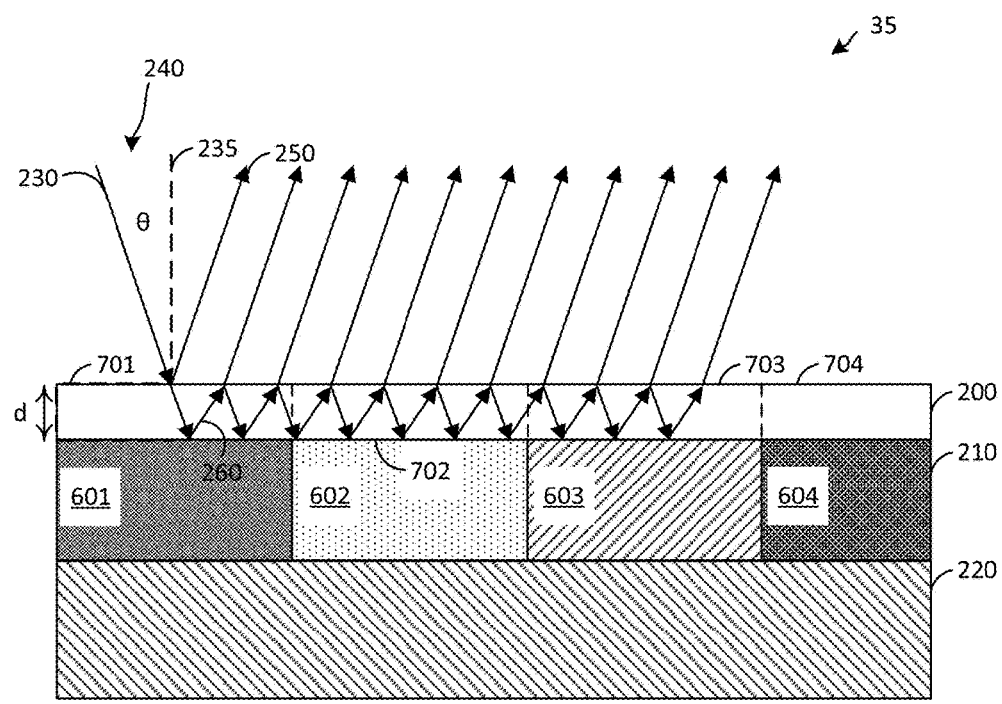
FIG. 6 is a cross sectional view depicting an exemplary embodiment of a reflection optical filter having a layer comprising a plurality of opaque metals.

FIG. 6 depicts an exemplary embodiment of a reflection optical filter 35 in which the substrate 210 is segmented into different types of metals. Specifically, the substrate 210 comprises portions 601-604 where each potion 601-604 is composed of a different type of metal. As described above, the absorbed light 260 propagating through the silicon thin-film 200 penetrates a small distance into the portions 601-604. Since each portion 601-604 is composed of a different material, the distance that the light penetrates each respective portion 601-604 is slightly different. Thus, a portion 701 of the silicon thin-film 200 formed on the substrate portion 601 will have different resonance wavelengths than the film portions 702-704 formed on the substrate portions 602-604 respectively. Thus, the absorption peak wavelength in the light reflected from portion 701 will be different from the absorption peak wavelengths in the light reflected from the other portions 702-704 such that the light reflected from the portion 701 will have a different color relative to the light reflected by the other portions 702-704. Similarly, the light reflected from each respective portion 702-704 will have a different color relative to the light reflected by the other portions of the silicon thin-film 200. Thus, by patterning the substrate 210 with different metal materials, any desired image may be reflected from the surface of the silicon thin-film 200. In the example shown by FIG. 6, four portions 601-604 are depicted, but the substrate 210 can be configured to have any number of portions 601-604 reflecting different colors of light in other embodiments.

Figure 7:
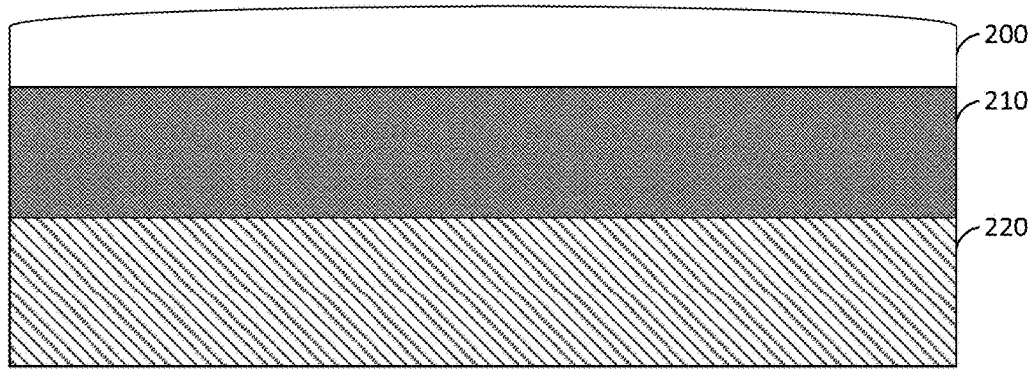
FIG. 7 is a cross sectional view depicting an exemplary embodiment of a reflection optical filter having a curved surface.

Note that the dielectric film 200 shown by FIG. 2A and FIG. 6 has a generally flat surface profile, but other profiles of the film 200 are possible. In one embodiment, the film 200 has a curved surface profile, such as is depicted by FIG. 7. In this regard, the thickness of the film 200 varies across a width of the filter 35 to define a curvature on the surface of the film 200. Thus, across the curvature, the absorption peak at one point of the surface is different than at a different point such that different colors are exhibited by the light reflecting from the two points. Therefore, the resulting thickness variations produces a variation of colors reflected by the optical filter 35 across the surface of the silicon thin-film 200, as described above. Note that it is possible for a portion of the silicon thin-film to be flat and for other portions of the silicon thin-film to be non-flat, as may be desired.

In various embodiments described above, the layer 200 is described as a silicon thin-film. However, as noted above, other types of layers 200 are possible. As an example, it is possible for the layer 200 to be composed of other high refractive index semiconductor or dielectric materials and for the substrate 210 to be composed of other metals such as titanium, chromium, copper, silver, and etc. The techniques of controlling the color of light reflected by the filter 35 by controlling the thickness of the layer 200, annealing the layer 200, and/or selecting the material of the substrate metal 210 are applicable for different types of filters 35, including layers 200 of different materials.

In some embodiments, a semi-transparent layer may be formed on the thin film 200 in order to reduce the amount of light that enters into the thin film 200. In order to minimize the overall thickness of the structure, an ultra-thin layer having a thickness of around 4 nm to 10 nm may be used for the semi-transparent layer, but other types of semi-transparent layers may be possible in other embodiment. By reducing the amount light that enters the thin film 200 through the use of the semi-transparent layer, less light must be absorbed by the thin film 200 in order to achieve critical coupling, as will be described in more detail hereafter. Thus, by using such a semi-transparent layer, the thickness of the thin film 200 can be reduced in order to achieve near perfect absorption of a given wavelength relative to an embodiment that does not employ a semi-transparent layer on the thin film 200.

Figure 8:
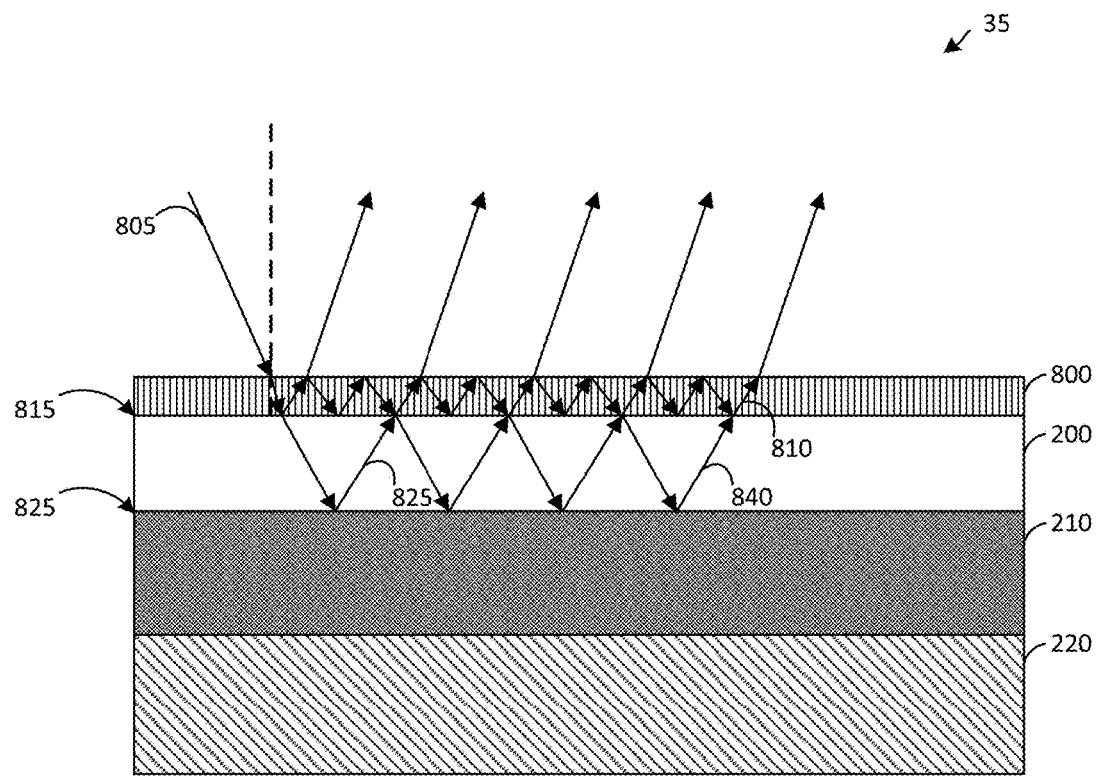
FIG. 8 is a cross sectional view depicting an exemplary embodiment of a reflection optical filter having a layer comprising a percolated metal.

FIG. 8 depicts a cross sectional view of an exemplary embodiment of a reflection optical filter 35 having a semi-transparent ultra-thin film 800. In the embodiment of FIG. 8, the optical filter 35 is substantially the same as the filter shown by FIG. 2A, except as will be described hereafter. The filter 35 of FIG. 8 has a semi-transparent ultra-thin film 800 positioned above thin-film 200. As in FIG. 2A, the thin-film 200 may be positioned adjacent to an opaque metal layer 210, and the opaque metal layer 210 may be positioned adjacent to a substrate 220. In an exemplary embodiment, the semi-transparent ultra-thin film 800, thin-film 200, and opaque metal layer 210 collectively form an optical cavity for filtering light.

In an exemplary embodiment, the semi-transparent ultra-thin film 800 may reflect a portion of an incident light wave 805 (i.e., photons), absorb a portion of the light, and permit a portion of the light to pass through to the silicon thin-film 200. A first portion of the light 810 may be reflected at a first boundary 815 between the semi-transparent ultra-thin film 800 and thin-film 200 (i.e., reflected by a surface of the thin-film 200), and another portion of light 825 may pass through the thin film 200 and be reflected at a second boundary 815 between the thin-film 200 and opaque metal layer 210 (i.e., a surface of the opaque metal layer 210). Some of the light 825 escapes the thin film 200 and propagates though the ultra-thin film 800 as the light 825 reflects back-and-forth in the thin film 200 between the surfaces of the opaque metal layer 210 and the semi-transparent ultra-thin film 800. Other portions of the light 825 are completely absorbed by the thin film 200. In one embodiment, the configuration of the optical cavity, including the thickness of the thin film 200 and the index of refraction of the thin film 200, is selected such that critical coupling occurs within the thin film 200 for the wavelength being absorbed. As known in the art, critical coupling generally refers to a condition in which an amount of light (e.g., optical energy) that enters an optical cavity equals an amount of light lost (e.g., absorbed by the optical cavity) during one trip of the light through the optical cavity (e.g., from film 800 to the layer 210 and back to the film 800). The critical coupling condition occurs when a wavelength of light matches an optical resonance mode of an optical cavity such that near perfect absorption of the wavelength of light occurs. When a wavelength matches the optical cavity's optical resonance mode, light at the matching wavelength may resonate within, but not leave, the optical cavity. Thus, the optical cavity may nearly completely absorb the wavelength of light (e.g., by critical coupling of the wavelength to the resonance mode). An optical cavity's resonance mode may correspond to attributes of the optical cavity, including characteristics of materials of the optical cavity (e.g., conductivity) and optical cavity thickness.

In addition, a wavelength of light incident on an optical filter may experience a phase delay as the light passes across boundaries between different materials in the optical filter. In an embodiment, a phase delay of a wavelength of light may result from each of the reflections at the first boundary 815, the reflection at the second boundary 825, and propagation within the thin-film 200. A total "round-trip" phase delay for a wavelength of light entering the optical cavity may be determined using the following equation:

$$\varphi_{total} = \varphi_s - (\varphi_{21} + \varphi_{23})$$

where $\varphi_{total}$ represents round-trip phase delay, $\varphi_s$ represents phase delay from propagation within the thin-film 200, $\varphi_{21}$ represents phase change caused by reflection at the first boundary 810, and $\varphi_{23}$ represents phase change caused by reflection at the second boundary 815.

When to total is equal to zero and critical coupling of the light to a zeroth order fundamental Fabry-Perot resonance mode may cause near perfect light absorption of light at the corresponding wavelength. Thus, near perfect absorption of light may occur at a wavelength corresponding to a zeroth order optical resonance mode of the optical cavity, and may form an absorption peak at the wavelength in light reflected from a surface of the thin-film 200 (i.e., at the boundary 810).

As noted herein, varying a thickness of the silicon thin-film 200 varies a wavelength at which near perfect light absorption (i.e., critical coupling of the wavelength of light to a zeroth order optical resonance mode of the optical cavity) occurs in the optical filter 35. Adding the semi-transparent ultra-thin film 800 above the silicon thin-film 200 may allow a thinner silicon thin-film 200 to be used for optical filter 35 while still achieving near perfect light absorption (i.e., critical coupling of light) for a desired wavelength. Stated differently, addition of the semi-transparent ultra-thin film 800 may reduce the ratio of required optical cavity thickness to absorption wavelength for the optical filter 35. In some embodiments, addition of a semi-transparent ultra-thin film 800 as described herein may allow a reflection optical filter 35 to have an optical cavity with a thickness that is approximately one order of magnitude less than a wavelength for which absorption may be desired (e.g., $\frac{1}{14}$ of the wavelength). Other embodiments of optical filter 35 without a semi-transparent ultra-thin film 800 may require a thicker optical cavity to achieve absorption of the desired wavelength (e.g., a thickness $\frac{1}{5}$ of the wavelength). Thus, addition of semi-transparent ultra-thin film 800 may allow for reduction of an overall thickness of the optical filter 35 and, specifically, the thin film 200 while still achieving near perfect light absorption of a desired wavelength.

In some embodiments, semi-transparent ultra-thin film 800 may substantially minimize reflectivity of light at a desired wavelength while simultaneously limiting transmission of light to the thin-film 200 so that critical coupling of the desired wavelength to the zeroth order Fabry-Perot resonance mode within the optical cavity is achieved. Reflectivity of the semi-transparent ultra-thin film 800 may be minimized (e.g., significantly reduced) based on a thickness of the film 800. In some embodiments, spaces or holes located between clusters of molecules of the ultra-thin film 800 may allow the light to pass through to the thin-film 200, such as when the ultra-thin film 800 is a percolated material. The ultra-thin film 800 may have a thickness that is close to but above a percolation threshold for the material. Below the percolation threshold, the ultra-thin film 800 may include disconnected clusters instead of a uniform film. In this regard, the material may have a dielectric optical property. Above the percolation threshold, clusters of the ultra-thin film 800 may become connected, the ultra-thin film 800 may exhibit optical properties of an effective material. In some embodiments, the ultra-thin film 800 may not have the same optical properties as thicker metal films; in other words, optical properties of the ultra-thin film 800 may depend on a thickness of the ultra-thin film 800. For example, as the thickness of the ultra-thin film 800 increases, more light is reflected and less light penetrates through the ultra-thin film 800. By adjusting the thickness of the ultra-thin film 800, a percentage of light penetrating through the ultra-thin film 800 can be adjusted, and critical coupling of the incident light to the fundamental optical resonance mode of the optical cavity can be realized at a specific wavelength. The optical cavity includes the ultra-thin film 800 as a partial reflecting mirror, the thin film 200 between the ultra-thin film 800 and the substrate 210, and the substrate 210. At the critical coupling condition, light at one wavelength is completely absorbed in the optical cavity. Light with nearby wavelengths is partially absorbed and reflected. When the critical coupling condition is not met, the light is partially reflected and partially absorbed in the optical cavity. The reflectivity and absorption depend on wavelength.

Note that, while the ultra-thin film 800 may be any suitable material for achieving the functionality of the optical filter 35 described herein, in an exemplary embodiment, the semi-transparent ultra-thin film 800 may be a percolated metal (e.g., aluminum, silver, gold, titanium, etc.). It has been observed that the desired absorption occurs when ultra-thin film 800 has metallic properties (e.g., electric conductivity). In some embodiments, the ultra-thin film 800 may absorb a portion of optical energy of the light incident on filter 35 (e.g., by conducting electrons), with the thin film 200 and the metal layer 210 absorbing substantially all of the remaining optical energy. In other embodiments, ultra-thin film 800 may comprise other suitable materials, (e.g., graphene, molybdenum disulfide, tin oxide, etc.) for partially transmitting and partially reflecting light. In some embodiments, ultra-thin film 800 may include two-dimensional materials of single-layer or multiple layer for achieving desired functionality.

In some embodiments, the semi-transparent ultra-thin film 800 may reduce the amount of light passing through to the optical cavity and thin-film 200 of optical filter 35 (e.g., by reflecting or absorbing portions of the light). Semi-transparent ultra-thin film 800 may be a quasi-continuous layer with small voids through which light can pass. In some embodiments, semi-transparent ultra-thin film 800 may comprise a percolated metal, but other materials (e.g., graphene, molybdenum disulfide, tin oxide, etc.) may be possible in other embodiments. For example, a metal having a suitable index of refraction (e.g., aluminum, gold, silver, etc.) may be suitable for use in semi-transparent ultra-thin film 800. In an exemplary embodiment, semi-transparent ultra-thin film 800 may be percolated aluminum, and may have a thickness suitable for achieving the properties of semi-transparent ultra-thin film 800 and functionality of optical filter 35 described herein. For example, a percolated aluminum semi-transparent ultra-thin film 800 may have a thickness in a range between approximately 4-10 nm. A thickness of less than approximately 4 nm generally results in clusters that are too far apart to have the properties, which may be desired in order to achieve a desired resonance mode within the optical cavity to enable critical coupling to the desired wavelength. As described above, a thickness greater than about 10 nm may result in a significantly higher reflectivity of the ultra-thin film 800, preventing light from passing through the ultra-thin film 800 (i.e., making the ultra-thin film 800 opaque). In one embodiment, the ultra-thin film 800 may have a thickness of about 7 nm resulting in a percolated (quasi-continuous) film 800 with a desired reflectivity minimum close to zero. In other embodiments, semi-transparent ultra-thin film 800 may comprise any of a variety of materials suitable for limiting or reducing light transmission to the thin-film 200, and other thicknesses of the semi-transparent ultra-thin film 800 may be possible.

Note also that, in some embodiments, thin-film 200 may be any suitable material and have any suitable thickness for achieving critical coupling of a desired wavelength to a zeroth order resonance mode within an optical cavity of optical filter 35. In an exemplary embodiment, thin-film 200 comprises silicon, and may be thermally annealed. In other embodiments, thin-film 200 may comprise other materials, such as another kind of semiconductor, or a dielectric material. As noted above, a thickness of the thin-film 200 may range between 30 and 60 nm, but other thicknesses are possible.

Figure 9:
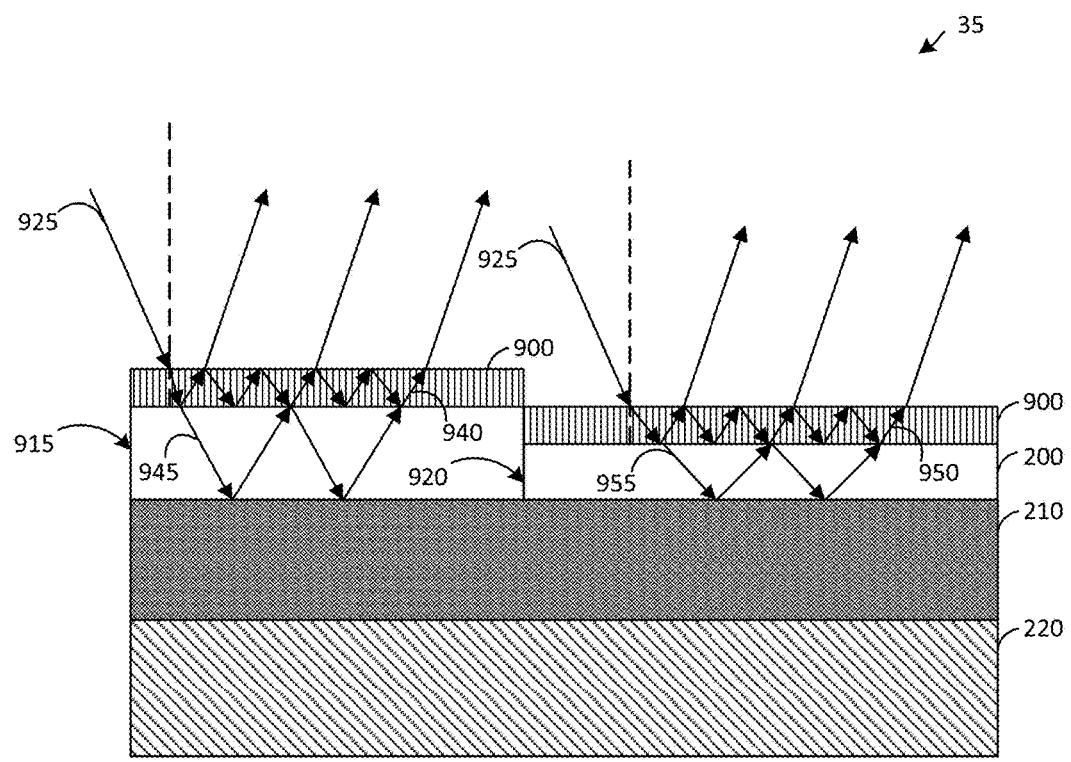
FIG. 9 is a cross sectional view depicting an exemplary embodiment of a reflection optical filter having a semi-transparent ultra-thin film deposited on a thin-film with a plurality of sections of varying thicknesses for filtering different wavelengths of incident light.

FIG. 9 depicts a cross-sectional view of an embodiment of a reflection optical filter 35 having a semi-transparent ultra-thin film 900 deposited on a thin-film 200 with a plurality of sections 915 and 920 of varying thicknesses for filtering different wavelengths of incident light 925. As described hereinabove, a peak wavelength of light absorbed by an optical cavity comprising ultra-thin film 900, thin-film 200 and opaque metal layer 210 can be altered (e.g., tuned) by varying the thickness of thin-film 200. Absorption of different wavelengths by the optical filter 35 may allow reflection of different colors by the same optical filter 35 (e.g., when optical filter 35 may be used for creating visible images, designs, etc.). In the embodiment of FIG. 9, the optical filter 35 is substantially the same as the filter shown by FIG. 2B, except that the optical filter 35 of FIG. 9 has an ultra-thin film 900 deposited across each of the plurality of sections 915 and 920. As in FIG. 2B, the thin-film 200 of FIG. 9 has been deposited on an opaque metal layer 210, which is positioned adjacent to a substrate 220.

Although other configurations and characteristics (e.g., dimensions, materials, etc.) of optical filter 35 may be possible in other embodiments, in the embodiment of FIG. 9, thin-film 200 comprises two sections 915 and 920 for absorbing two different wavelengths of light 905 incident on ultra-thin film 900. A reflection optical filter 35 according to other embodiments may comprise any number of sections 915 and 925 and corresponding thicknesses.

In some embodiments, the optical filter 35 of FIG. 9 may have an optical cavity comprising ultra-thin film 900, thin-film 200 and opaque metal layer 210. However, an effective cavity length of the optical filter 35 may vary according to thicknesses of the various layers of the optical cavity (e.g., variation in thicknesses of sections 915 and 920 of thin-film 200). Thus, a portion of optical filter 35 having one or more layers that are thicker than another portion of optical filter 35 may have a longer effective cavity length than the other portion. For example, an effective cavity length of the portion of optical filter 35 comprising section 915 of thin-film 200 may be longer than an effective cavity length of the portion of optical filter 35 comprising section 920 of thin-film 200. In this regard, a wavelength absorbed with an optical cavity of optical filter 35 (e.g., a wavelength which may experience a critical coupling condition within the optical cavity) may vary according to effective cavity length, as described above.

As described above with regard to FIG. 8, the semi-transparent ultra-thin film 900 may reflect a portion of an incident light wave 925, absorb a portion of the light, and permit a portion of the light to pass through to thin-film 200. In an optical cavity formed by the layers of optical filter 35 including section 915, a first portion of the light 940 may be reflected at a first boundary between the semi-transparent ultra-thin film 900 and thin-film 200 (i.e., reflected by a surface of the thin-film 200), while another portion of light 945 may pass through the thin-film 200 and be reflected at a second boundary between the thin-film 200 and opaque metal layer 210 (i.e., a surface of the opaque metal layer 210). Some of the light 940 propagates though the ultra-thin film 900 as the light 945 reflects back-and-forth in the thin-film 200 between the surfaces of the opaque metal layer 210 and the semi-transparent ultra-thin film 900. Other portions of the light 945 are completely absorbed by section 915 of the thin-film 200. Thus an absorption peak may be formed at a first resonance wavelength in an optical cavity formed by the layers of optical filter 35 including section 915.

Likewise, in an optical cavity formed by the layers of optical filter 35 including section 920, an absorption peak may be formed at a second resonance wavelength that may be different from the first resonance wavelength absorbed by the optical cavity including section 915. A first portion of the light 950 may be reflected at a first boundary between the semi-transparent ultra-thin film 900 and thin-film 200 (i.e., reflected by a surface of the thin-film 200), while another portion of light 955 may pass through the thin-film 200 and be reflected at a second boundary between the thin-film 200 and opaque metal layer 210 (i.e., a surface of the opaque metal layer 210). Some of the light 950 propagates though the ultra-thin film 900 as the light 955 reflects back-and-forth in the thin-film 200 between the surfaces of the opaque metal layer 210 and the semi-transparent ultra-thin film 900. Other portions of the light 955 are completely absorbed by section 920 of the thin-film 200. Thus, each optical cavity formed by layers of optical filter 35 including sections 915 and 920 may nearly completely absorb a respective first and second wavelengths of light (e.g., by critical coupling of incident light to the resonance mode).

Figure 10:
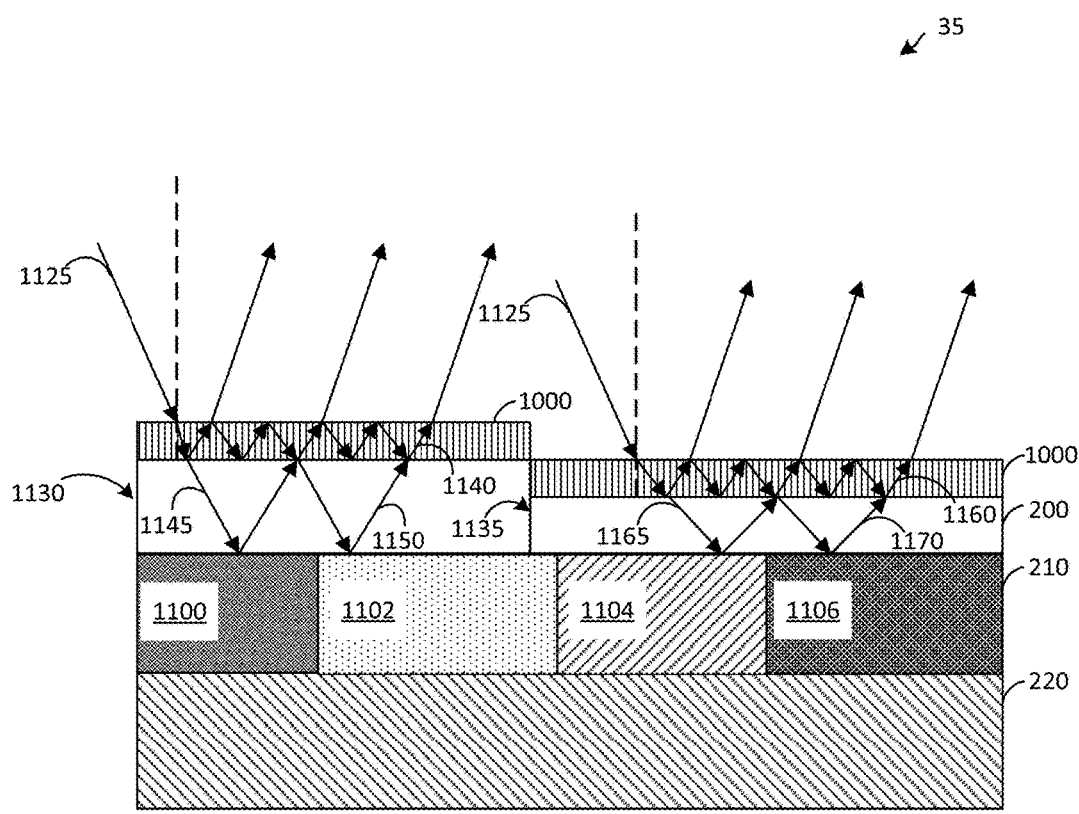
FIG. 10 is a cross sectional view depicting an exemplary embodiment of a reflection optical filter having a semi-transparent ultra-thin film and thin-film deposited on an opaque layer having a plurality of sections positioned on a substrate.

FIG. 10 depicts a cross sectional view of an embodiment of a reflection optical filter 35 having a semi-transparent ultra-thin film 1000 and thin-film 200 deposited on an opaque layer 210 having a plurality of sections 1100, 1102, 1104 and 1106 positioned on a substrate 220. The embodiment of FIG. 10 is similar to the embodiment depicted by FIG. 6, except that the optical filter of FIG. 10 comprises an ultra-thin film 1000, a thin-film 200 with varying thicknesses, and the opaque layer 210 with a plurality of sections 1100, 1102, 1104 and 1106. As described above with regard to FIG. 6, an amount of opaque layer 210 light penetrates varies according to absorptive properties of each material in sections 1100, 1102, 1104 and 1106.

Although ultra-thin film 1000 and thin-film 200 may absorb a majority of incident light 1125 that is absorbed within an optical cavity of optical filter 35, in some embodiments, an amount of incident light 1125, however small, may be absorbed by opaque layer 210. Absorption by opaque layer 210 may affect an amount of optical energy remaining (e.g., from incident light 1125) for absorption within the optical cavity of optical filter 35. Specifically, an amount of light absorbed by opaque layer 210 may affect (e.g., shorten) an effective optical cavity length of optical filter 35. Thus, the amount of light opaque layer 210 absorbs may vary according to optical properties of a material selected for opaque layer 210. In this regard, a wavelength of incident light 1125 at which an absorption peak occurs within the optical cavity of optical filter 35 may be altered by selecting a different material for opaque layer 210. Using this technique, material for opaque layer 210 may be selected to tune optical filter 35 so that absorption of a desired wavelength is achieved.

Note that, in the embodiment of FIG. 10, thin-film 200 has two sections 1130 and 1135 with two different thicknesses, similar to the embodiment depicted by FIG. 9. As with the optical filter 35 depicted by FIG. 9, the optical filter 35 depicted by FIG. 10 may filter different wavelengths of light based on a configuration of the optical filter 35 (e.g., thickness of layers such as ultra-thin film 1000, thin-film 200, or otherwise). Importantly, as demonstrated by FIG. 10, a reflection optical filter 35 may comprise a combination of ultra-thin film 1000, a thin-film 200 having one or more sections 1130 and 1135 of varying thicknesses, and an opaque layer 210 comprising a plurality of sections 1100, 1102, 1104 and 1106. As described above, a wavelength of light 1125 absorbed by the optical filter 35 may be tuned by varying a thickness of thin-film 200. By adding an opaque layer 210 comprising a plurality of sections 1100, 1102, 1104 and 1106, additional configurations of optical filter 35 may be possible while achieving near perfect absorption at a desired wavelength. For example, in an embodiment, varying a thickness of a section of thin-film 200 (e.g., section 1130 or 1135) may vary a wavelength absorbed by the optical filter 35. Varying a material of opaque layer 210 beneath thin-film 200 may further vary the wavelength absorbed by the optical filter 35 (e.g., by varying an effective cavity length of the optical cavity). In this regard, such variations may yield near perfect absorption at multiple desired wavelengths in a number of section areas.

In some embodiments, each of sections 1100, 1102, 1104 and 1106 of opaque layer 210 may comprise a different material (e.g., aluminum, gold, silver, etc.) having optical properties for achieving absorption of a desired wavelength of incident light 1125 within an optical cavity of optical filter 35. In an exemplary embodiment, each of sections 1100, 1102, 1104 and 1106 of opaque layer 210 may comprise a different metal, but sections 1100, 1102, 1104 and 1106 may comprise any material or combination of materials in other embodiments.

Discussion will now turn to examples of functionality of optical filter 35 in embodiments in which opaque layer 210 may comprise a plurality of sections comprising a plurality of materials (e.g., sections 1100, 1102, 1104 and 1106). In some embodiments, portions of light may be absorbed by each of section 1130 and 1135 of thin-film 200, and within each of sections 1130 and 1135, a plurality of portions of light may be absorbed by sections 1100, 1102, 1104 and 1106, wherein each of sections 1100, 1102, 1104 and 1106 comprises a different metallic material (e.g., aluminum, gold, silver, etc.). For example, a portion of light 1140 may be absorbed by ultra-thin film 1000, with an additional portion of light 1145 absorbed by section 1130 of thin-film 200 and section 1100 of opaque layer 210. Another portion of light 1150 may be absorbed within thin-film 200 and section 1102. In section 1135, a portion of light 1160 may be absorbed within ultra-thin film 1000, with an additional portion 1165 absorbed within thin-film 200 and section 1104 of opaque layer 210. Another portion of light 1170 may be absorbed within thin-film 200 and section 1106. In this regard, in the embodiment of FIG. 10, two different portions of light 1140 and 1160 may be absorbed by ultra-thin film 1000, two additional portions of light 1145 and 1165 may be absorbed within thin-film 200 and sections 1100 and 1104, respectively. Two other portions of light 1150 and 1170 may be absorbed within thin-film 200 and section 1102 and 1106 respectively. Each of the different portions of light absorbed within the optical filter 35 of FIG. 10 may correspond to a wavelength of incident light 1125; thus, an absorption peak may be formed within optical filter 35 at wavelengths corresponding to different portions of light absorbed. In other embodiments, other configurations or compositions of optical filter 35 may be possible for achieving the desired absorption, including variation of thicknesses, materials, surface profiles, or other characteristics of any or a combination of ultra-thin film 1000, thin-film 200, opaque layer 210, or substrate 220.

Now, therefore, the following is claimed:

1. A reflection optical filter for filtering light incident on the reflection optical filter, comprising:
   an opaque substrate;
   a first layer formed on the opaque substrate; and
   a semi-transparent layer formed on the first layer, wherein the first layer is between the semi-transparent layer and the opaque substrate, the semi-transparent layer having a thickness sufficiently thin such that at least a portion of the incident light passes through the semi-transparent layer to the first layer,
   wherein the portion of the incident light passes through the first layer and reflects from the opaque substrate and includes light at a wavelength, wherein the opaque substrate, the first layer, and the semi-transparent layer form an optical cavity for filtering the incident light, wherein the wavelength corresponds to an optical resonance mode of the optical cavity, and wherein the first layer has an index of refraction and a thickness such that the light at the wavelength is absorbed in the optical cavity, thereby forming an absorption peak at the wavelength in the incident light.

2. The reflection optical filter of claim 1, wherein the semi-transparent layer comprises a percolated metal film.

3. The reflection optical filter of claim 2, wherein the percolated metal film comprises aluminum.

4. The reflection optical filter of claim 1, wherein the semi-transparent layer comprises graphene.

5. The reflection optical filter of claim 1, wherein a thickness of the semi-transparent layer is between 4.0 nanometers and 7.0 nanometers.

6. The reflection optical filter of claim 1, wherein the first layer comprises a semiconductor material.

7. The reflection optical filter of claim 1, wherein the first layer comprises a dielectric material.

8. The reflection optical filter of claim 1, wherein the opaque substrate comprises metal.

9. The reflection optical filter of claim 8, wherein a total roundtrip phase delay of an optical wave in the optical cavity is zero.

10. The reflection optical filter of claim 1, wherein the optical resonance mode of the optical cavity is the zeroth order optical resonance.

11. The reflection optical filter of claim 1, wherein the semi-transparent layer comprises a metal and has a thickness less than 10 nanometers.

12. A reflection optical filter for filtering light incident on the reflection optical filter, comprising:
   an opaque substrate;
   a first layer formed on the opaque substrate; and
   a semi-transparent layer formed on the first layer, wherein the first layer is between the semi-transparent layer and the opaque substrate, the semi-transparent layer having a thickness sufficiently thin such that a portion of the incident light passes through the semi-transparent layer to the first layer, wherein the portion of the incident light passes through the first layer and reflects from the opaque substrate and includes light at a wavelength, wherein the opaque substrate, the first layer, and the semi-transparent layer form an optical cavity for filtering the incident light, and wherein the first layer has an index of refraction and a thickness such that critical coupling for the wavelength of the light occurs in the optical cavity thereby forming an absorption peak at the wavelength in the incident light.

13. The reflection optical filter of claim 12, wherein the semi-transparent layer comprises a percolated metal film.

14. The reflection optical filter of claim 13, wherein the percolated metal film comprises aluminum.

15. The reflection optical filter of claim 12, wherein the semi-transparent layer comprises graphene.

16. The reflection optical filter of claim 12, wherein a thickness of the semi-transparent layer is between 4.0 nanometers and 7.0 nanometers.

17. The reflection optical filter of claim 12, wherein the first layer comprises a semiconductor material.

18. The reflection optical filter of claim 12, wherein the first later comprises a dielectric material.

19. The reflection optical filter of claim 12, wherein the opaque substrate comprises metal.

20. A method for filtering light, comprising:
   providing a reflection optical filter having an opaque substrate, a first layer formed on the opaque substrate, and a semi-transparent layer formed on the first layer, wherein the first layer is between the semi-transparent layer and the opaque substrate;
   passing, through the semi-transparent layer to the first layer, a portion of light incident on the reflection optical filter;
   passing, through the first layer, the portion of the incident light including light at a wavelength;
   reflecting the portion of the incident light from the opaque substrate; and
   filtering the light with an optical cavity formed by the opaque substrate, the first layer, and the semi-transparent layer, wherein the wavelength corresponds to an optical resonance mode of the optical cavity, wherein the first layer has an index of refraction and a thickness such that the light at the wavelength is absorbed in the optical cavity, thereby forming an absorption peak at the wavelength in the incident light.

21. The method of claim 20, wherein the semi-transparent layer comprises a percolated metal film.

22. The method of claim 20, wherein a thickness of the semi-transparent layer is between 4.0 nanometers and 7.0 nanometers.

* * * * *